United States Patent [19]

Hasson

[11] Patent Number: 5,129,896
[45] Date of Patent: Jul. 14, 1992

[54] HOLDER TO FACILITATE USE OF A LASER IN SURGICAL PROCEDURES

[76] Inventor: Harrith M. Hasson, P.O. Box 14898, Chicago, Ill. 60614

[21] Appl. No.: 752,162

[22] Filed: Aug. 22, 1991

Related U.S. Application Data

[63] Continuation of Ser. No. 436,070, Nov. 13, 1989, abandoned.

[51] Int. Cl.$^5$ .............................................. A61N 5/06
[52] U.S. Cl. .................................. 606/15; 606/16; 606/17
[58] Field of Search ........................ 606/14–17, 606/7, 9; 128/397, 398

[56] References Cited

U.S. PATENT DOCUMENTS

| | | | |
|---|---|---|---|
| 3,834,391 | 9/1974 | Block | 606/9 |
| 3,982,541 | 9/1976 | L'Esperance | 606/14 X |
| 4,211,229 | 7/1980 | Wurster | 606/14 |
| 4,313,431 | 2/1982 | Frank | 606/16 X |
| 4,503,853 | 3/1985 | Ota et al. | 606/16 |
| 4,519,390 | 5/1985 | Horne | 606/15 |
| 4,592,353 | 6/1986 | Daikuzono | 606/17 X |
| 4,819,630 | 4/1989 | DeHart | 606/16 X |
| 4,834,093 | 5/1989 | Littleford et al. | 128/398 X |
| 4,865,029 | 9/1989 | Pankratov et al. | 128/398 X |
| 4,950,266 | 8/1990 | Sinofsky | 606/15 |

FOREIGN PATENT DOCUMENTS

| | | | |
|---|---|---|---|
| 0070459 | 1/1983 | European Pat. Off. | 606/16 |
| 2147209 | 5/1985 | United Kingdom | 606/16 |

*Primary Examiner*—Lee S. Cohen
*Attorney, Agent, or Firm*—Wood, Phillips, Van Santen, Hoffman & Ertel

[57] ABSTRACT

An instrument of the type having a casing with a leading edge to be engaged with tissue that is to be laser treated, a laser fiber with a body having an emitting end, and structure for mounting the laser fiber to the casing so that the emitting end of the laser fiber is in a fixed position with respect to the casing and thereby a tissue that is to be treated and engaged by the leading end of the casing.

31 Claims, 1 Drawing Sheet

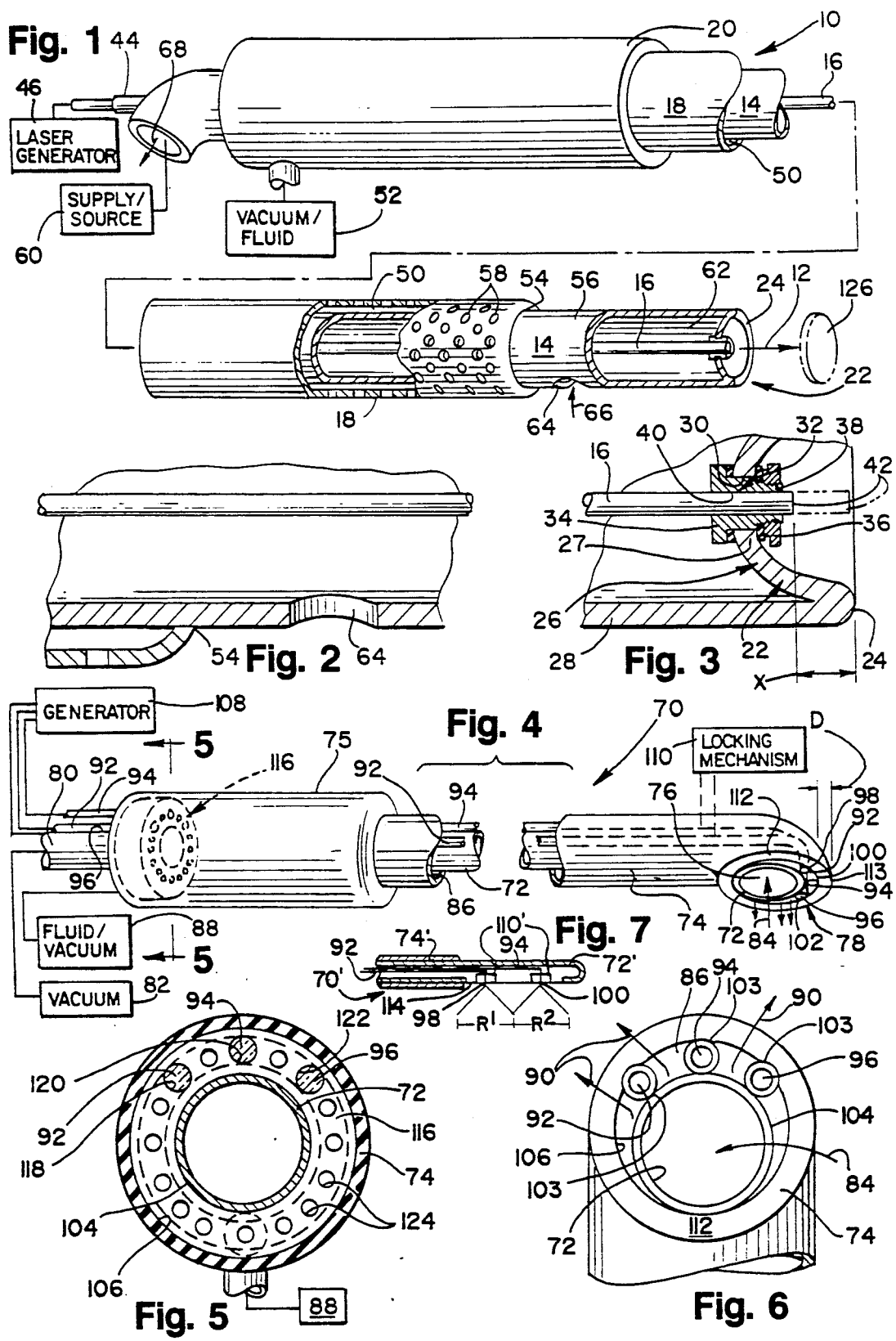

HOLDER TO FACILITATE USE OF A LASER IN SURGICAL PROCEDURES

This application is a continuation of application Ser. No. 436,070, filed Nov. 13, 1989, now abandoned.

BACKGROUND OF THE INVENTION

1. Field of the Invention

This invention relates to lasers of the type used in surgical procedures and, more particularly, to a holder for maintaining a laser fiber in a predetermined position relative to tissue to be laser treated.

2. Background Art

Endometrial laser ablation is now recognized as an alternative to treatment of certain uterine diseases by the performance of a hysterectomy. Among the many advantages of laser assisted surgery are the ability to precisely destroy localized areas of body tissue, excellent hemostasis, rapid healing of treated tissue with minimal discomfort to a patient, and reduced expense compared to similar procedures performed by alternative, conventional techniques.

Conventional laser surgery requires the use of a hysteroscope, which is a multi-purpose instrument that is inserted into a uterine cavity that has been previously distended with a fluid medium. The hysteroscope accommodates optical equipment and a laser fiber which is used to transmit laser energy to the endometrial tissues. The fluid medium serves multiple purposes In addition to distending the uterus, it cools the laser and can be used as a vehicle to carry away debris accumulated during the performance of a surgical procedure.

There are two generally recognized techniques for using lasers in surgical procedures—dragging and blanching. With the dragging technique, the laser fiber is drawn directly against and across tissue to be treated. In blanching, the emitting end of the laser fibers is maintained at a predetermined distance from a tissue and moved more slowly relative to the tissue than with the dragging technique to allow the treated tissue to change in color, in the case of an endometrial surface, from pink to white. More laser power is required in blanching procedures than in dragging procedures.

While laser surgery has been very successful, the performance thereof can be time consuming and occasionally hazardous to the patient when performed by conventional methods and employing conventional equipment. Lengthy operations can result in dangerous amounts of the distending fluid being absorbed into the body.

Constant observance of the location of the emitting end of the laser fiber is also required with conventional equipment to keep the laser fiber in a proper relationship with the tissue that is being treated thereby. Location of the emitting end of the laser too far away from the tissue can make it ineffective, whereas holding of the laser fiber too close to tissue may cause underlying tissue to be damaged and/or the laser fiber to be irreparably burned, which frequently results in a part of the fiber breaking off within a body cavity.

To observe the laser location during surgical procedures, optical instruments are introduced to the cavities in which the tissue is to be treated. The need for optical equipment complicates the surgical procedures by requiring additional space for the accommodation of optical fibers. Optical equipment is also difficult to use effectively within the body cavities. The fluid medium used to distend the cavity commonly becomes cloudy during the performance of surgical procedures. When this occurs, the procedure must be interrupted to allow the clouding to diminish.

Another problem with conventional procedures is that the emitting end of the laser fiber is frequently accidentally brought into contact with the tissue which it is treating during a blanching procedure. Because of the high power requirements for blanching, the emitting end of the laser can burn up and fall off after recurring contact with the tissue. The surgical procedure must then be interrupted to replace the fiber, refurbish it by polishing, and/or remove the broken off fragments of the fibers.

Another problem with conventional laser equipment is that it generally requires use by one with a high degree of skill.

A still further drawback with conventional techniques is that they may take a considerable period of time to perform. It is common to use a single laser fiber in conventional equipment. Consequently, the user thereof must make repeated passes of the laser over the tissue to be treated. This is time consuming and difficult to accomplish, and often undesirably results in certain tissue areas being repeatedly passed over by the laser beam.

A still further drawback with conventional laser structures is that they do not lend themselves to treatment of all surfaces on body cavities. In fact, certain of the body cavity surfaces may be entirely inaccessible to conventional laser equipment. One configuration of laser equipment is generally inadequate for treatment of all cavities contemplated to be treated by the laser. For example, certain surfaces in the uterus are in such a confined space that it is impossible to perform a blanching technique without the laser fiber contacting the endometrial tissues.

SUMMARY OF THE INVENTION

The present invention has, as its principal objectives, the provision of a laser structure that permits efficient, safe, and effective performance of laser surgery in virtually all body cavities in which laser treatment is appropriate.

More particularly, the present invention comprehends an instrument of the type having a casing with a leading edge to be engaged with tissue that is to be laser treated, a laser fiber with a body having an emitting end, and structure for mounting the laser fiber to the casing so that the emitting end of the laser fiber is in a fixed position with respect to the casing and thereby a tissue that is to be treated and engaged by the leading end of the casing.

In a preferred form, the laser fiber is adjustably mounted to the casing so that the laser fiber can be selectively fixed in a plurality of different positions with respect to the casing and consistently held in an optimum position during surgery. The result is that tissue damage is controlled to produce consistent tissue treatment.

The invention contemplates, among other configurations, at least two arrangements for the laser fiber to facilitate access to virtually all conceivable tissue in the human body to be treated during laser surgery. The first configuration is a frontal arrangement. With this arrangement, a casing, which is preferably elongate and cylindrical, has an annular free edge which can be abutted against a tissue to be treated. The edge preferably resides in a single plane that is transverse to, and preferably perpendicular to, the axis of the casing. The laser fiber is mounted to the casing so that the emitting end thereof emits laser energy in the line of the casing axis from the leading end of the casing. A recessed wall portion is provided on the casing for a mechanism to lock the laser fiber(s) in any of a number of different positions. The fiber emitting end is preferably adjustable to a point up to where it coincides with the plane of the leading edge of the casing.

In an alternative, lateral form of the invention, the casing supports the fiber so that the fiber emits energy in a line transverse to the length of the casing. In one form of the invention, the casing is formed with a right angle bend at its leading end. The leading casing edge in this configuration resides preferably in a plane that is generally parallel to the length of the casing.

The invention also contemplates the accommodation of multiple laser fibers which are simultaneously useable. In the latter described, lateral version, the emitting ends of the fibers are preferably spaced lengthwise of the casing. Each laser fiber emitting end produces a generally conical beam pattern. The laser fibers are strategically located so that the pattern from adjacent laser fibers overlaps so that as the instrument is moved relative to a tissue, a large area can be treated simultaneously by the plural fibers.

Because of the controlled relationship between the emitting end of the fiber and tissue to be treated, the surgery can be performed without observing the inside of the body cavity, thereby obviating the need for optical equipment and thereby reducing the complexity of the surgical equipment.

The invention contemplates the provision of a sleeve to cooperate with the casing to define a first flow channel for fluid to be introduced into a cavity, within which the instrument resides, or withdrawn from that cavity. Preferably, the casing is hollow and defines a second, internal fluid flow channel. The first and second flow channels can be cooperatively arranged so that saline, or other appropriate fluid, can be circulated into and out of the cavity in which the instrument resides. A vacuum source and fluid supply can be selectively attached to the first and second flow channels to direct the fluid into and out of the cavity to thereby cool the laser fibers and pick up and remove debris developed in the performance of the surgical operation.

In one form of the invention, the sleeve has a forward end that closely surrounds the casing to close the first flow channel. A plurality of openings are provided through the sleeve to permit a shower of fluid to be introduced to the cavity. The casing has a larger opening therethrough between the forward end of the sleeve and the leading end of the casing. The large opening can accommodate relatively large pieces of debris which are drawn by suction through the casing hollow to a point of disposal and permits rapid injection and withdrawal of fluid from a cavity. By obviating the need for optical equipment, space otherwise occupied by the optical equipment can be used to circulate the cooling/flushing fluid. In the event that optical equipment is employed, the high rate of fluid circulation possible allows blood, tissue, and debris to be rapidly and continuously removed to leave the fluid clear for viewing therethrough in the cavity.

The inventive structure, by reason of its permitting efficient performance of laser surgical procedures, minimizes the exposure time of the patient to the distending fluid in the cavity in which the surgery is performed.

In one form of the invention, the laser fibers are located within the first flow channel.

The invention also contemplates the use of a lens mounted to the casing and/or sleeve to control the dispersion of a laser beam emitted by the laser fiber.

The invention contemplates also that the sleeve and casing can be economically made to be disposable.

BRIEF DESCRIPTION OF THE DRAWINGS

FIG. 1 is a perspective view of an instrument for performing laser surgery according to the present invention, with part of the instrument broken away to reveal a cooperating casing and sleeve that support a laser fiber and cooperatively provide a fluid circulating path;

FIG. 2 is an enlarged, fragmentary, section view of a part of the instrument in FIG. 1 at a point where the casing and sleeve are joined;

FIG. 3 is an enlarged, fragmentary, section view of the leading end of the casing showing the connection between the casing and a laser fiber;

FIG. 4 is a perspective view of a modified form of instrument for performing laser surgery according to the present invention;

FIG. 5 is a section view of the modified instrument taken along line 5—5 of FIG. 4;

FIG. 6 is an enlarged side elevation view of the leading end of the instrument of FIG. 4; and FIG. 7 is a schematic representation of a casing with a plurality of laser fibers and showing resulting laser beam patterns.

DETAILED DESCRIPTION OF THE DRAWINGS

In FIGS. 1-3, a preferred form of instrument, according to the present invention, for performing laser surgery, is shown at 10. The instrument 10 is termed a frontal instrument, as it is intended for direction of a laser beam forwardly in the direction of arrows 12 from the front of the instrument 10 against a tissue to be treated. The instrument has particular utility for treatment of tissue remote from the point of entry and in confined spaces.

The instrument 10 consists of a casing 14, to which a laser fiber 16 is mounted, a cylindrical sleeve 18, surrounding the casing in coaxial relationship therewith, and a handle 20 surrounding the sleeve 18 to facilitate manipulation of the instrument 10.

The casing 14 has a leading end 22 with a leading, annular edge 24, which is intended to be brought into contact with body tissue in the area that is to be treated by the laser. The leading end 22 of the casing 14 has a wall 26, with a flat portion 27, spaced rearwardly of the edge 24, to which the end of the laser fiber 16 is mounted. The wall 26 defines a cup shape, opening forwardly, and blends into the cylindrical, peripheral wall 28 of the housing 14 so as to afford a blunt rim defining the forwardly annular casing edge 24, which edge 24 resides substantially within a single plane.

The wall portion 27 has a through bore 30 of large enough diameter to accommodate a fiber locking mechanism 32 and the fiber 16. The locking mechanism 32 consists of a male part 34, which is directed forwardly through the bore 30, and a female part 36, which is threadably engaged with that portion 38 of the male part 34 projecting through and exposed forwardly of the wall portion 27. The male part 38 is radially compressed upon the female part 36 being threaded thereonto so as to firmly embrace the fiber 16. This compression feature may be afforded by providing longitudinal slits in the male part 38 to define deformable flaps which are radially collapsed by the female part 36.

The described locking mechanism 32 permits the fiber 16 to be moved lengthwise of the casing 14 to situate the emitting end 42 of the fiber 16 in a desired relationship with the plane defined by the edge 24. Preferably, the fiber end 42 is adjustable from the solid line position in FIG. 3 to the phantom position in that same figure. The distance between these two positions is designated X and is preferably on the order of 1 millimeter. In the latter position, the fiber end 42 is flush with the plane of the edge 24 so that the instrument can be used to perform the earlier described dragging technique. With the fiber end 42 in the solid line position, the instrument 10 can be used to perform surgery using the blanching technique. The position of the fiber end 42 can be optimally selected and maintained depending upon the nature of the tissue and treatment.

The fiber 16 extends coaxially through the casing 14 along substantially the entire length thereof and projects from a socket 44 at the trailing end of the casing 14. The laser fiber 16 is powered by a conventional laser generator, shown schematically at 46 in FIG. 1.

The invention also contemplates the circulation of fluid, which is preferably saline, into and out of the cavity surrounded by the tissue that is being laser treated. The debris that is developed through the procedure can thus be continuously flushed from the body cavity. At the same time, the circulating fluid dislodges debris that adheres to the tissue during a surgical procedure and also cools the laser fiber 16, to prevent it from overheating, which might necessitate its repair and/or replacement.

The casing 14 and sleeve 18 cooperatively accommodate the fluid. The space between the casing 14 and sleeve 18 defines a first fluid flow channel 50 which, at its trailing end, is connected to either a source of vacuum or a fluid supply, shown schematically at 52 in FIG. 1.

The forward edge 54 of the sleeve 18 closely frictionally grips the outer surface 56 of the casing 14, so as to close the forward end of the first flow channel 50. Adjacent the forward edge 54 of the sleeve 18, a plurality of radially projecting apertures is provided. The apertures 58 are preferably arranged in annular rows, with the apertures 58 in each row equidistantly spaced around the circumference of the sleeve 18 and the rows spaced equidistantly axially along the length of the sleeve 18. As can be seen in FIG. 1, fluid from a supply 52 flows into the flow channel 50 and is dispersed in a shower through the apertures 58 to the cavity within which the instrument 10 resides. One or more of the apertures 58 can be obliquely arranged to produce a more random fluid shower.

The casing 14 can be connected at its trailing end to a source of vacuum or a liquid supply, shown schematically at 60 in FIG. 1. The interior of the casing 14 is hollow and defines a second flow channel 62 communicating with the supply/source 60. The casing 14, between the forward edge 54 of the sleeve 18 and leading edge 24 of the casing 14, has an enlarged opening 64 which communicates with the flow path 62. With a source of vacuum at 60, fluid and debris flow into the second flow chamber through the opening 64 in the direction of arrow 66, travel lengthwise of the casing 14 and exhaust in tee direction of arrow 68 at the trailing end of the instrument 10 for appropriate disposition. The above arrangement can be used to circulate a fluid, such as saline, in which a conventional laser beam will be operable. The saline will cool the laser fiber 16 and, as described above, serves as the medium to pick up and transport debris from the operating site to an appropriate point of disposal.

The dimensions of the casing 14, sleeve 18, apertures 58 and opening 64 are chosen depending upon the desired rate of fluid circulation. Because the need for optical equipment is obviated by the invention, the instrument 10 can permit a high rate of fluid flow in a compact configuration. This rapid circulation of fluid accounts for efficient cooling of the instrument 10.

The invention contemplates facilitated, inexpensive manufacture of the sleeve 18 and casing 14 so that the structure is disposable after each use.

An alternative embodiment of the invention is shown at 70 in FIGS. 4-6. The instrument 70 has a casing 72, a surrounding sleeve 74, and a handle 75 corresponding to the embodiment in FIGS. 1-3. The casing 72 is hollow to define a flow path 76 between a leading end 78 and a trailing end 80 thereof. The trailing end 80 of the casing 72 communicates with a source of vacuum or a fluid supply, indicated schematically at 82. With the flow path 76 communicating with the source of vacuum 82, fluid and material flows in the direction of arrows 84 into and through the casing 72 to the vacuum source 82.

The sleeve 74 cooperates with the casing 72 to define an outer flow channel 86 communicating with a source of vacuum or fluid supply, identified schematically at 88. In the event of a fluid supply 88, the fluid is directed forwardly through the channel 86 and out from between the casing 72 and sleeve 74, as indicated by arrows 90 at the leading end 78 of the instrument 70.

There are two principal differences between the instrument 70 in FIG. 4 and that in FIG. 1. First, the instrument 70 in FIG. 4 carries a plurality of fibers 92, 94, 96. Secondly, the leading end 78 of the instrument 70 is turned at a right angle so that the emitting ends 98, 100, 102 of the fibers 92, 94, 96, consecutively, direct a laser beam at right angles to the axial extent of the instrument 70. The invention contemplates that the angle of the turned end 78 of the instrument can be changed from that shown, depending upon the configuration of the cavity in which the surgery is to be performed.

The fibers 92, 94, 96 are received in guide tubes 103, which are bent into L-shapes to conform to the general configuration of the casing 14 and sleeve 18, which tubes 103 are, in turn, captively maintained between the outer surface 104 of the casing 72 and the inner surface 106 of the sleeve 74. The fibers 92, 94, 96 are powered by a conventional generator, shown schematically at 108 in FIG. 4. Cooling fluid flowing in channel 86 flows against the fibers 92, 94, 96 to effect cooling thereof. The invention also contemplates the elimination of the guide tubes 103 whereby the fibers 92, 94, 96 are exposed directly to the fluid in channel 86 for more efficient cooling thereof.

The relationship between the emitting ends 98, 100, 102 and the casing 72 and sleeve 74 is selectively fixed by fiber locking mechanisms, such as that described and shown schematically at 110 in FIG. 4. Preferably, the fibers 92, 94, 96 are adjustable selectively relative to the casing 72 between a) a first portion in which the ends 98, 100, 102 reside in the plane defined by a planar guiding surface 112, which can be dragged against a tissue to be treated, and b) a second position approximately 1 millimeter radially inside of the plane of the surface 112. Preferably, the forwardmost fiber emitting end 100 is spaced at least approximately 2 mm from the axially forwardmost edge 113 of the instrument 70.

Accordingly, fluid introduced from the supply 88 flows in the channel 86 into the body cavity and out of the cavity into the flow channel 76 and back to the evacuation source 82 for appropriate disposal. The fluid flow direction can be reversed by communicating the supply 88 with the channel 76 and the evacuation source 82 with the channel 86.

The invention also contemplates variations of the location of the emitting ends 98, 100, 102 of the fibers 92, 94, 96 from that shown in FIGS. 4-6. In FIG. 7, two of the fibers 92, 94 are shown schematically in association with a casing 72' and sleeve 74', correspond to the casing 72 and sleeve 74 in the embodiment in FIGS. 4-6. The emitting ends 98, 100 on the fibers 92, 94 respectively, project through or are immediately radially inwardly of an opening 114 in casing 72'. The emitting ends 98, 100 are spaced axially with respect to the casing 72'. The spacing between the ends 98, 100 is chosen so that the dispersion radius for the laser beam for the fiber 92, designated R1, coincides with the dispersion radius R2 for the fiber 94. With the arrangement in FIG. 7, approximately twice the surface area can be treated compared to an instrument having a single fiber for a given movement of the instrument.

An optional spacing washer is shown at 116 in FIGS. 4 and 6. The spacing washer 116 resides radially between the surfaces 104, 106 on the casing and sleeve 72, 74, respectively. The washer 116 has bores 118, 120, 122 to accept the fibers 92, 94, 96 and associated guide tubes (not shown in FIG. 5) and maintain a desired spacing between the fibers 92, 94, 96. The washer 116 has a plurality of peripherally spaced bores 124 therethrough which communicate between the supply 88 and the flow channel 86.

A further modification of the invention is the optional provision of a lens 126 (FIG. 1) at the leading end of the instruments 10, 70, to control the dispersion of the laser beam from the fibers 16, 92, 94, 96.

The foregoing disclosure of specific embodiments is intended to be illustrative of the broad concepts comprehended by the invention.

I claim:

1. An instrument for performing laser surgery, said instrument comprising:
   a casing having a leading end,
   said leading end having an edge that is integrally formed with the casing and can be engaged with tissue that is to be laser treated;
   a laser fiber having an emitting end; and
   means for mounting the laser fiber to the casing so that the emitting end of the laser fiber is in a predetermined fixed position with respect to the casing edge and thereby a tissue to be laser treated that is engaged by the edge at the leading end of the casing,
   said laser mounting means including a cup-shaped wall opening in a leading direction,
   said cup-shaped wall defining a recess in which the emitting end of the laser fiber can be situated,
   said cup-shaped wall diverging in a leading direction with respect to the casing leading end and thereby permitting laser energy to diverge outwardly from the emitting end of the laser fiber without being directed against the casing as might potentially cause damage to the instrument,
   wherein said edge at the leading end has an annular, uninterrupted configuration.

2. The instrument for performing laser surgery according to claim 1 wherein said mounting means comprises means for adjustably mounting the laser fiber to the casing so that the laser fiber can be selectively fixed in a plurality of positions with respect to the casing edge and a tissue to be laser treated.

3. The instrument for performing laser surgery according to claim 1 wherein said casing end is at one axial end of the casing.

4. The instrument for performing laser surgery according to claim 1 wherein said casing has a hollow cylindrical configuration and the laser fiber is in substantially coaxial relationship with the casing.

5. The instrument for performing laser surgery according to claim 1 wherein said leading edge is an annular edge residing in a single plane and is integral with the cup-shaped wall.

6. An instrument for performing laser surgery, said instrument comprising:
   a casing having a leading end,
   said leading end having an edge that is integrally formed with the casing and can be engaged with tissue that is to be laser treated;
   a laser fiber having an emitting end; and
   means for mounting the laser fiber to the casing so that the emitting end of the laser fiber is in a predetermined fixed position with respect to the casing edge and thereby a tissue to be laser treated that is engaged by the edge at the leading end of the casing,
   said laser mounting means including a cup-shaped wall opening in a leading direction,
   said cup-shaped wall defining a recess in which the emitting end of the laser fiber can be situated,
   said cup-shaped wall diverging in a leading direction with respect to the casing leading end and thereby permitting laser energy to diverge outwardly from the emitting end of the laser fiber without being directed against the casing as might potentially cause damage to the instrument,
   wherein the casing has a substantially cylindrical configuration with axial ends and there is a sleeve in coaxial axially overlapping relationship with the casing, there being a first fluid flow channel defined between the sleeve and casing, said casing being hollow to define a second fluid flow channel.

7. The instrument for performing laser surgery according to claim 6 wherein the sleeve has a forward end spaced axially rearwardly of said leading casing end and there is a first opening in the casing between the forward end of the sleeve and the leading casing end communicating with said second flow channel.

8. The instrument for performing laser surgery according to claim 7 wherein one of said sleeve and casing has a plurality of radially extending openings therethrough, said plurality of openings each being smaller than the first opening.

9. The instrument for performing laser surgery according to claim 6 wherein one axial end of the sleeve closely engages the casing to close one axial end of the first flow channel.

10. The instrument for performing laser surgery according to claim 6 including means for connecting a source of vacuum to at least one of said first and second flow channels.

11. The instrument for performing laser surgery according to claim 6 including means for connecting a fluid supply to at least one of said first and second flow channels.

12. The instrument for performing laser surgery according to claim 6 wherein the laser fiber resides in the first flow channel.

13. The instrument for performing laser surgery according to claim 6 including means for circulating a fluid into one of the first and second flow channels and out of the other of the first and second flow channels.

14. An instrument for performing laser surgery, said instrument comprising:
a casing having a leading end,
said leading end having an edge that is integrally formed with the casing and can be engaged with tissue that is to be laser treated;
a laser fiber having an emitting end; and
means for mounting the laser fiber to the casing so that the emitting end of the laser fiber is in a predetermined fixed position with respect to the casing edge and thereby a tissue to be laser treated that is engaged by the edge at the leading end of the casing,
said laser mounting means including a cup-shaped wall opening in a leading direction,
said cup-shaped wall defining a recess in which the emitting end of the laser fiber can be situated,
said cup-shaped wall diverging in a leading direction with respect to the casing leading end and thereby permitting laser energy to diverge outwardly from the emitting end of the laser fiber without being directed against the casing as might potentially cause damage to the instrument,
said instrument including a lens and means for attaching the lens to the casing to control dispersion of a beam emitted by said laser fiber.

15. An instrument for facilitating the performance of laser surgery, said instrument comprising:
a casing having a forward leading end and a trailing end,
said leading end having an edge that can be engaged with tissue that is to be laser treated;
a laser fiber having an emitting end; and
means for mounting the laser fiber to the casing so that the emitting end of the laser fiber is in a predetermined fixed position with respect to the casing edge and thereby a tissue to be laser treated that is engaged by the edge at the leading end of the casing,
wherein said casing has an elongate wall with a cylindrical configuration, there is an opening in the casing cylindrical wall defining a radial passageway through the cylindrical wall with respect to the axis of the cylindrical wall and the means for mounting the laser fiber mounts the laser fiber so that the laser fiber emits energy through the casing wall opening at a position between the leading end and the trailing end of the casing and does not project forwardly beyond the leading end of the casing and the emitting end of the laser fiber emits a beam in a direction transverse to the length of the casing.

16. The instrument for performing laser surgery according to claim 15 wherein the leading end of the casing is closed to prevent emission of a laser beam therethrough.

17. An instrument for performing laser surgery, said instrument comprising:
a casing having a leading end,
said leading end having an edge that can be engaged with tissue that is to be laser treated;
a laser fiber having an emitting end; and
means for mounting the laser fiber to the casing so that the emitting end of the laser fiber is in a predetermined fixed position with respect to the casing edge and thereby a tissue to be laser treated that is engaged by the edge at the leading end of the casing,
wherein the casing has a substantially cylindrical configuration with axial ends and there is a sleeve in coaxial axially overlapping relationship with the casing, there being a first fluid flow channel defined between the sleeve and casing, said casing being hollow to define a second fluid flow channel,
wherein there is a guide tube for accepting the laser fiber and said guide tube has a portion extending lengthwise of the casing and an end that is bent at an angle to the guide tube portion.

18. An instrument for performing laser surgery comprising:
a casing having a forward leading end and a trailing end,
said leading end having an edge that can be engaged with tissue that is to be laser treated;
a laser fiber having an emitting end; and
means for mounting the laser fiber to the casing so that the emitting end of the laser fiber is in a predetermined fixed position with respect to the casing edge and thereby a tissue to be laser treated that is engaged by the edge at the leading end of the casing,
wherein the casing has an elongate configuration and the means for mounting the laser fiber mounts the laser fiber at a position between the leading end and the trailing end of the casing so that the laser fiber does not project forwardly beyond the leading end of the casing and the emitting end of the laser fiber emits a beam in a direction transverse to the length of the casing,
wherein there are a plurality of laser fibers and means for mounting the plurality of laser fibers to the casing so that beams emitted thereby are directed transverse to the length of the casing.

19. An instrument for performing laser surgery, said instrument comprising:
a casing having a leading end,
said leading end having an edge that can be engaged with tissue that is to be laser treated;
first and second laser fibers each having an emitting end; and
means for mounting each laser fiber to the casing so that the emitting end of each laser fiber is in a predetermined fixed position with respect to the casing edge and thereby a tissue to be laser treated that is engaged by the edge at the leading end of the casing,
wherein the casing has a substantially cylindrical configuration with axial ends and there is a sleeve in coaxial axially overlapping relationship with the casing, there being a first fluid flow channel defined between the sleeve and casing, said casing being hollow to define a second fluid flow channel, wherein the sleeve has a forward end spaced axially rearwardly of said leading casing end and there is a first opening ion the casing between the forward end of the sleeve and the leading casing end communicating with said second flow channel, wherein one of said sleeve and casing has a plurality of radially extending openings therethrough, said plurality of openings each being smaller than the first opening, wherein the first and second laser fibers have their emitting ends spaced lengthwise of the casing.

20. An instrument for performing laser surgery, said instrument comprising:

a casing having a leading end and a trailing end, said leading end having a continuous, uninterrupted, curved, leading edge that can be engaged with tissue that is to be laser treated; and means for adjustably mounting a laser fiber to the casing so that an emitting end of a laser fiber can be fixed in a plurality of preselected positions with respect to the casing and thereby a tissue to be laser treated in a range between a first position wherein the emitting end of a laser fiber is flush with the edge at the leading end of the casing and a second position wherein the emitting end of a laser fiber is spaced rearwardly with respect to said casing from its first position, said curved leading edge facilitating guided sliding movement relative to a surface against which the leading edge bears.

21. The instrument for performing laser surgery according to claim 20 wherein said casing has a cup-shaped recess at its leading end opening and diverging in a leading direction and a part of said laser fiber resides in said recess.

22. The instrument for performing laser surgery according to claim 20 wherein said casing has an elongate configuration, there is a wall on the casing that is spaced lengthwise of the casing from the leading edge thereon and the laser fiber mounting means adjustably fixes the laser fiber to the wall.

23. The instrument for performing laser surgery according to claim 20 in combination with a laser fiber.

24. The instrument for performing laser surgery according to claim 23 wherein the emitting end of the laser fiber is directly exposed at the leading end of the casing so that the emitting end of the laser fiber can be dragged along tissue by dragging the edge at the leading end of the casing along a tissue with the laser fiber in its first position.

25. The instrument for performing laser surgery according to claim 20 including means associated with the casing for introducing fluid into a cavity in which a surgical procedure is being performed to facilitate laser treatment of tissue in said cavity.

26. The instrument for performing laser surgery according to claim 20 including means associated with the casing for circulating fluid into and removing fluid from a cavity in which a surgical procedure is being performed to facilitate laser treatment of tissue in said cavity.

27. An instrument for performing laser surgery, said instrument comprising:

an elongate casing having a leading end and a trailing end, said leading end having an edge that can be engaged with tissue that is to be laser treated;

first and second laser fibers each having an emitting end; and means for mounting the laser fibers to the casing so that the emitting ends of the laser fibers can be placed in a predetermined fixed position with respect to the casing edge and in spaced relationship to each other and a tissue to be laser treated that is engaged by the edge at the leading end of the casing, said mounting means mounting the laser fibers to the casing between the leading and trailing ends thereof so that the emitting end of each of the first and second fibers is aligned to emit energy in a line transverse to the length of the casing, whereby laser energy impinging on the tissue is a combination of energy from the first and second laser fibers and the tissue area that is impinged upon by the first and second laser fibers to greater than the area that is impinged upon by either of the first and second laser fibers alone.

28. The instrument for performing laser surgery according to claim 27 wherein the emitting ends of the first and second laser fibers are spaced from each other along a line between the casing ends.

29. An instrument for performing laser surgery, said instrument comprising:

a casing having an elongate, substantially straight, cylindrical configuration with a forward leading end and a trailing end spaced in a lengthwise direction and an opening at a location spaced from the leading and trailing ends thereof, said casing have an edge that can be engaged with tissue that is to be laser treated;

a laser fiber having an emitting end; and means for mounting the laser fiber to the casing so that the laser fiber emits energy through the casing opening and the emitting end of the laser fiber is in a predetermined fixed position with respect to the casing edge between the leading end and the trailing end so that the emitting end is arranged to emit energy transversely to the length of the casing between the leading end and the trailing end thereof and the emitting end of the laser fiber does not project forwardly beyond the leading end of the casing.

30. The instrument for performing laser surgery according to claim 29 wherein the casing is substantially straight over substantially its entire extent between the leading end and trailing end thereof.

31. An instrument for facilitating the performance of laser surgery, said instrument comprising:

a casing having a forward leading end and a trailing end, said leading end having an edge that can be engaged with tissue that is to be laser treated;

a laser fiber having an emitting end; and means for mounting the laser fiber to the casing so that the emitting end of the laser fiber is in a predetermined fixed position with respect to the casing edge and thereby a tissue to be laser treated that is engaged by the edge at the leading end of the casing, wherein said casing has a substantially straight cylindrical wall defining the leading end thereof, there is an opening in the cylindrical wall at a location spaced from the leading end thereof, and the means for mounting the laser fiber mounts the laser fiber so that the laser fiber emits energy through cylindrical wall opening radially with respect to the axis of the cylindrical wall and so that the laser fiber does not project forwardly beyond the leading end of the casing.

* * * * *